(12) United States Patent
Surtees et al.

(10) Patent No.: US 6,858,740 B2
(45) Date of Patent: Feb. 22, 2005

(54) 2-OXO-1-PYRROLIDINE DERIVATIVES, PROCESS FOR PREPARING THEM AND THEIR USES

(75) Inventors: John Surtees, Watermael-Boisfort (BE); Violeta Marmon, Oxfordshire (GB); Edmond Differding, Ottignies-Louvain-la-Neuve (BE); Vincent Zimmermann, Lausanne (CH)

(73) Assignee: UCB Farchim S.A., Bulle (CH)

( * ) Notice: Subject to any disclaimer, the term of this patent is extended or adjusted under 35 U.S.C. 154(b) by 205 days.

(21) Appl. No.: 10/609,544

(22) Filed: Jul. 1, 2003

(65) Prior Publication Data

US 2004/0092576 A1 May 13, 2004

Related U.S. Application Data

(62) Division of application No. 10/204,275, filed as application No. PCT/EP01/01956 on Feb. 21, 2001.

(30) Foreign Application Priority Data

Feb. 23, 2000 (GB) .............................................. 0004297

(51) Int. Cl.⁷ ............................................. C07D 207/04
(52) U.S. Cl. ....................... 548/550; 548/146; 548/253; 549/59; 549/473; 546/276.4; 502/150
(58) Field of Search ................................ 548/550, 146, 548/253; 546/276.4; 549/59, 473

(56) References Cited

U.S. PATENT DOCUMENTS 4,997,955 A    3/1991   Merger et al.

FOREIGN PATENT DOCUMENTS

| DE | 92 031 | 8/1972 |
| EP | 0 162 036 | 11/1985 |

OTHER PUBLICATIONS

Goodall et al., Tetrahedron, NL, Elsevier Science Publishers, Amsterdam, vol. 52, No. 19, pp. 6739–6758 (1996).

Xingshu Li et al., Tetrahedron: Asymmetry, vol. 10, pp. 3863–3867 (1999).

Prous, Drugs of the Future, ES, Barcelona, vol. 19, No. 2, pp. 111–113 (1994).

*Primary Examiner*—Rita Desai
*Assistant Examiner*—Golam M M Shameem
(74) *Attorney, Agent, or Firm*—Wenderoth, Lind & Ponack, LLP

(57) ABSTRACT

The invention concerns 2-oxo-1-pyrrolidine derivatives and a process for preparing them and their uses. The invention also concerns a process for preparing α-ethyl-2-oxo-1-pyrrolidine acetamide derivatives from unsaturated 2-oxo-1-pyrrolidine derivatives. Particularly the invention concerns novel intermediates and their use in methods for the preparation of S-α-ethyl-2-oxo-1-pyrrolidine acetamide.

7 Claims, No Drawings

2-OXO-1-PYRROLIDINE DERIVATIVES, PROCESS FOR PREPARING THEM AND THEIR USES

This is a divisional of Ser. No. 10/204,275, filed Aug. 20, 2002, which is a 371 of PCT/EP01/01956, filed Feb. 21, 2001.

The invention concerns 2-oxo-1-pyrrolidine derivatives and a process for preparing them and their uses. The invention also concerns a process for preparing α-ethyl-2-oxo-1-pyrrolidine acetamide derivatives from unsaturated 2-oxo-1-pyrrolidine derivatives.

Particularly the invention concerns novel intermediates and their use in methods for the preparation of (S)-(−)-α-ethyl-2-oxo-1-pyrrolidine acetamide, which is referred under the International Nonproprietary Name of Levetiracetam, its dextrorotatory enantiomer and related compounds. Levetiracetam is shown as having the following structure:

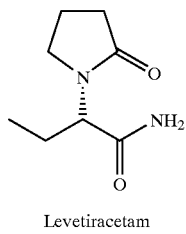

Levetiracetam

Levetiracetam, a laevorotary compound is disclosed as a protective agent for the treatment and the prevention of hypoxic and ischemic type aggressions of the central nervous system in the European patent No. 162036. This compound is also effective in the treatment of epilepsy, a therapeutic indication for which it has been demonstrated that its dextrorotatory enantiomer (R)-(+)-α-ethyl-2-oxo-1-pyrrolidine acetamide completely lacks activity (A. J. GOWER et al., Eur. J. Pharmacol., 222. (1992), 193–203). Finally, in the European patent application No. 0 645 139 this compound has been disclosed for its anxiolytic activity.

The asymmetric carbon atom carries a hydrogen atom (not shown) positioned above the plane of the paper. The preparation of Levetiracetam has been described in the European patent No. 0162 036 and in the British patent No. 2 225 322, both of which are assigned to the assignee of the present invention. The preparation of the dextrorotatory enantiomer (R)-(+)-α-ethyl-2-oxo-1-pyrrolidine acetamide has been described in the European patent No. 0165 919. Nevertheless, these approaches do not fully satisfy the requirements for an industrial process. Therefore, a new approach has been developed via the asymmetric hydrogenation of new precursors.

In one expect, the invention provides a compound having the general formula (A) and pharmaceutically acceptable salts thereof.

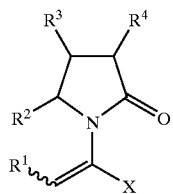

(A)

wherein X is —CONR$^5$R$^6$ or —COOR$^7$ or —CO—R$^8$ or CN;

R$^1$ is hydrogen or alkyl, aryl, heterocycloalkyl, heteroaryl, halogen, hydroxy, amino. nitro, cyano;

R$^2$, R$^3$, R$^4$, are the same or different and each is independently hydrogen or halogen, hydroxy, amino, nitro, cyano, acyl, acyloxy, sulfonyl, sulfinyl, alkylamino, carboxy, ester, ether, amido, sulfonic acid, sulfonamide, alkylsulfonyl, arylsulfonyl, alkoxycarbonyl, alkylsulfinyl, arylsulfinyl, alkylthio, arylthio, alkyl, alkoxy, oxyester, oxyamido, aryl, arylamino, aryloxy, heterocycloalkyl, heteroaryl, vinyl;

R$^5$, R$^6$, R$^7$ are the same or different and each is independently hydrogen, hydroxy, alkyl, aryl, heterocycloalkyl, heteroaryl, alkoxy, aryloxy; and R$^8$ is hydrogen, hydroxy, thiol, halogen, alkyl, aryl, heterocycloalkyl, heteroaryl, alkylthio, arylthio.

The term alkyl as used herein, includes saturated monovalent hydrocarbon radicals having straight, branched or cyclic moieties or combinations thereof and contains 1–20 carbon atoms, preferably 1–5 carbon atoms. The alkyl group may optionally be substituted by 1 to 5 substituents independently selected from the group consisting halogen, hydroxy, thiol, amino, nitro, cyano, acyl, acyloxy, sulfonyl, sulfinyl, alkylamino, carboxy, ester, ether, amido, sulfonic acid, sulfonamide, alkylsulfonyl, arylsulfonyl, alkoxycarbonyl, alkylsulfinyl, arylsulfinyl, alkylthio, arylthio, oxyester, oxyamido, heterocycloalkyl, heteroaryl, vinyl, (C1–C5) alkoxy, (C6–C10)aryloxy, (C6–C10)aryl. Preferred alkyl groups are methyl, ethyl, propyl, isopropyl, butyl, iso or ter-butyl, 2,2,2-trimethylethyl or the same substituted by at least a group selected from halogen, hydroxy, thiol, amino, nitro, cyano, such as trifluoromethyl, trichloromethyl, 2,2, 2-trichloroethyl, 1,1-dimethyl-2,2-dibromoethyl, 1,1-dimethyl-2,2,2-trichloroethyl.

The term "heterocycloalkyl", as used herein, represents an "(C1–C6)cycloalkyl" as defined above, having at least one O, S and/or N atom interrupting the carbocyclic ring structure such as tetrahydrofuranyl, tetrahydropyranyl, piperidinyl, piperazinyl, morpholino and pyrrolidinyl groups or the same substituted by at least a group selected from halogen, hydroxy, thiol, amino, nitro, cyano.

The term "alkoxy", as used herein includes —O-alkyl groups wherein "alkyl" is defined above. Preferred alkyl groups are methyl, ethyl, propyl, isopropyl, butyl, iso or ter-butyl, 2,2,2-trimethylethyl or the same substituted by at least a halo group such as trifluoromethyl, trichloromethyl, 2,2,2-trichloroethyl, 1,1-dimethyl-2,2-dibromoethyl. 1,1-dimethyl-2,2,2-trichloroethyl.

The term "alkylthio" as used herein, includes —S-alkyl groups wherein "alkyl" is defined above. Preferred alkyl groups are methyl, ethyl, propyl, isopropyl, butyl, iso or ter-butyl, 2,2,2-trimethylethyl or the same substituted by at least a halo group, such as trifluoromethyl, trichloromethyl, 2,2,2-trichloroethyl, 1,1-dimethyl-2,2-dibromoethyl, 1,1-dimethyl-2,2,2-trichloroethyl.

The term "alkylamino" as used herein, includes —NHalkyl or —N(alkyl)$_2$ groups wherein "alkyl" is defined above. Preferred alkyl groups are methyl, ethyl, n-propyl, isopropyl, butyl, iso or ter-butyl, 2,2,2-trimethylethyl or the same substituted by at least a halo group.

The term "aryl" as used herein, includes an organic radical derived from an aromatic hydrocarbon by removal of one hydrogen, such as phenyl, phenoxy, naphthyl, arylalkyl, benzyl, optionally substituted by 1 to 5 substituents independently selected from the group halogen, hydroxy, thiol, amino, nitro, cyano, acyl, acyloxy, sulfonyl, sulfinyl, alkylamino, carboxy, ester, ether, amido, sulfonic acid, sulfonamide, alkylsulfonyl, alkoxycarbonyl, alkylsulfinyl, alkylthio, oxyester, oxyamido, aryl, (C1–C6)alkoxy, (C6–C10)aryloxy and (C1–C6)alkyl. The aryl radical consists of 1–3 rings preferably one ring and contains 2–30 carbon atoms preferably 6–10 carbon atoms. Preferred aryl groups are, phenyl, halophenyl, cyanophenyl, nitrophenyl, methoxyphenyl, naphthyl, benzyl, halobenzyl, cyanobenzyl, methoxybenzyl, nitrobenzyl, 2-phenylethyl.

The term "arylamino" as used herein, includes —NHaryl or —N(aryl)$_2$ groups wherein "aryl" is defined above. Preferred aryl groups are, phenyl, halophenyl, cyanophenyl, nitrophenyl, methoxyphenyl, benzyl, halobenzyl, cyanobenzyl, methoxybenzyl, nitrobenzyl, 2-phenylethyl.

The term "aryloxy", as used herein, includes —O-aryl groups wherein "aryl" is defined as above. Preferred aryl groups are, phenyl, halophenyl, cyanophenyl, nitrophenyl, methoxyphenyl, benzyl, halobenzyl, cyanobenzyl, methoxybenzyl, nitrobenzyl, 2-phenylethyl.

The term "arylthio", as used herein, includes —S-aryl groups wherein "aryl" is defined as above. Preferred aryl groups are, phenyl, halophenyl, cyanophenyl, nitrophenyl, methoxyphenyl, benzyl, halobenzyl, cyanobenzyl, methoxybenzyl, nitrobenzyl, 2-phenylethyl.

The term "halogen", as used herein, includes an atom of Cl, Br, F, I,

The term "hydroxy", as used herein, represents a group of the formula —OH.

The term "thiol", as used herein, represents a group of the formula —SH.

The term "cyano", as used herein, represents a group of the formula —CN.

The term "nitro", as used herein, represents a group of the formula —NO$_2$.

The term "amino", as used herein, represents a group of the formula —NH$_2$.

The term "carboxy", as used herein, represents a group of the formula —COOH.

The term "sulfonic acid", as used herein, represents a group of the formula —SO$_3$H.

The term sulfonamide", as used herein, represents a group of the formula —SO$_2$NH$_2$.

The term "heteroaryl", as used herein, unless otherwise indicated, represents an "aryl" as defined above, having at least one O, S and/or N interrupting the carbocyclic ring structure, such as pyridyl, furyl, pyrrolyl, thienyl, isothiazolyl, imidazolyl, benzimidazol, tetrazolyl, pyrazinyl, pyrimidyl, quinolyl, isoquinolyl, isobenzofuryl, benzothienyl, pyrazolyl, indolyl, isoindolyl, purinyl, carbazolyl, isoxazolyl, thiazolyl, oxazolyl, benzthiazolyl, or benzoxazolyl, optionally substituted by 1 to 5 substituents independently selected from the group consisting hydroxy, halogen, thiol, amino, nitro, cyano, acyl, acyloxy, sulfonyl, sulfinyl, alkylamino, carboxy, ester, ether, amido, sulfonic acid, sulfonamide, alkylsulfonyl, alkoxycarbonyl, oxyester, oxyamido, alkoxycarbonyl, (C1–C5)alkoxy, and (C1–C5)alkyl.

The term "arylalkyl" as used herein represents a group of the formula aryl-(C1–C4alkyl)-. Preferred arylalkyl groups are, benzyl, halobenzyl, cyanobenzyl, methoxybenzyl, nitrobenzyl, 2-phenylethyl, diphenylmethyl, (4-methoxyphenyl)diphenylmethyl.

The term "acyl" as used herein, represents a radical of carboxylic acid and thus includes groups of the formula alky-CO—, aryl-CO—, heteroaryl-CO—, arylalkyl-CO—, wherein the various hydrocarbon radicals are as defined in this section. Preferred alkyl groups are methyl, ethyl, propyl, isopropyl, butyl, iso or ter-butyl, 2,2,2-trimethylethyl or the same substituted by at least a halo group. Preferred aryl groups are, phenyl, halophenyl, cyanophenyl, nitrophenyl, methoxyphenyl, benzyl, halobenzyl, cyanobenzyl, methoxybenzyl, nitrobenzyl, 2-phenylethyl.

The term "oxyacyl" as used herein, represents a radical of carboxylic acid and thus includes groups of the formula alky-CO—O—, aryl-CO—O—, heteroaryl-CO—O, arylalkyl-CO—O—, wherein the various hydrocarbon radicals are as defined in this section. Preferred alky and aryl groups are the same as those defined for the acyl group.

The term "sulfonyl" represents a group of the formula —SO$_2$-alkyl or —SO$_2$-aryl wherein "alkyl" and "aryl" are defined above. Preferred alkyl groups are methyl, ethyl, propyl, isopropyl, butyl, iso or ter-butyl, 2,2,2-trimethylethyl or the same substituted by at least a halo group. Preferred aryl groups are, phenyl, halophenyl, cyanophenyl, nitrophenyl, methoxyphenyl, benzyl, halobenzyl, cyanobenzyl, methoxybenzyl, nitrobenzyl, 2-phenylethyl.

The term "sulfinyl" represents a group of the formula —SO-alkyl or —SO-aryl wherein "alkyl" and "aryl" are defined above. Preferred alkyl groups are methyl, ethyl, propyl, isopropyl, butyl, iso or ter-butyl, 2,2,2-trimethylethyl or the same substituted by at least a halo group. Preferred aryl groups are, phenyl, halophenyl, cyanophenyl, nitrophenyl, methoxyphenyl, benzyl, halobenzyl, cyanobenzyl, methoxybenzyl, nitrobenzyl, 2-phenylethyl.

The term "ester" means a group of formula —COO-alkyl, or —COO-aryl wherein "alkyl" and "aryl", are defined above. Preferred alkyl groups are methyl, ethyl, propyl, isopropyl, butyl, iso or ter-butyl, 2,2,2-trimethylethyl or the same substituted by at least a halo group. Preferred aryl groups are, phenyl, halophenyl, cyanophenyl, nitrophenyl, methoxyphenyl, benzyl, halobenzyl, cyanobenzyl, methoxybenzyl, nitrobenzyl, 2-phenylethyl.

The term "oxyester" means a group of formula —COO-alkyl, or O—COO-aryl wherein "alkyl" and "aryl" are defined above. Preferred alkyl groups are methyl, ethyl, propyl, isopropyl, butyl, iso or ter-butyl, 2,2,2-trimethylethyl or the same substituted by at least a halo group. Preferred aryl groups are, phenyl, halophenyl, cyanophenyl, nitrophenyl, methoxyphenyl benzyl, halobenzyl, cyanobenzyl, methoxybenzyl, nitrobenzyl, 2-phenylethyl.

The term "ether" means a group of formula alky1O-alkyl or alkyl-O-aryl or aryl-O-aryl wherein "alkyl" a "aryl" are defined above. Preferred alkyl groups are methyl, ethyl, propyl, isopropyl, butyl, iso or ter-butyl, 2,2,2-trimethylethyl or the same substituted by at least a halo group. Preferred aryl groups are, phenyl, halophenyl, cyanophenyl, nitrophenyl, methoxyphenyl benzyl, halobenzyl, cyanobenzyl, methoxybenzyl, nitrobenzyl, 2-phenylethyl.

The term "amido" means a group of formula —CONH$_2$ or —CONHalkyl or —CON(alkyl)$_2$ or —CONHaryl or —CON(aryl)$_2$ wherein "alkyl1 and "aryl" are defined above. Preferably alkyl has 1–4 carbon atoms and aryl has 6–10 carbon atoms. Preferred alkyl groups are methyl, ethyl, propyl, isopropyl, butyl, iso or ter-butyl, 2,2,2-trimethylethyl or the same substituted by at least a halo group. Preferred aryl groups are, phenyl, halophenyl, cyanophenyl, nitrophenyl, methoxyphenyl, benzyl, halobenzyl, cyanobenzyl, methoxybenzyl, nitrobenzyl, 2-phenylethyl.

The term "oxyamido" means a group of formula O—CONH2 or —O—CONHalkyl or —O—CON(alkyl)2 or —O—CONHaryl or —O—CON(aryl)2 wherein "alkyl"

and "aryl" are defined above. Preferably alkyl has 1–5 carbon atoms and aryl has 6–8 carbon atoms. Preferred alkyl groups are methyl, ethyl, propyl, isopropyl, butyl, iso or ter-butyl, 2,2,2-trimethylethyl or the same substituted by at least a halo group. Preferred aryl groups are, phenyl, halophenyl. cyanophenyl, nitrophenyl, methoxyphenyl, benzyl, halobenzyl, cyanobenzyl, methoxybenzyl. nitrobenzyl, 2-phenylethyl.

Preferably $R^1$ is methyl, ethyl, propyl, isopropyl, butyl, iso or ter-butyl, 2,2,2-trimethylethyl or the same substituted by at least a halogen group such as trifluoromethyl trichloromethyl, 2,2,2trichloroethyl, 1,1-dimethyl-2,2-dibromoethyl, 1,1-dimethyl-2,2,2-trichloroethyl.

Preferably $R^2$, $R^3$ and $R^4$ are independently hydrogen or halogen or methyl, ethyl, propyl, isopropyl, butyl, iso or ter-butyl, 2,2,2-trimethylethyl or the same substituted by at least a halo group such as trifluoromethyl, trichloromethyl, 2,2,2-trichloroethyl, 1,1-dimethyl-2,2-dibromoethyl, 1,1-dimethyl-2,2,2-trichloroethyl.

Preferably $R^5$ and $R^6$ are independently hydrogen, methyl, ethyl, propyl, isopropyl, butyl, iso or ter-butyl, 2,2,2-trimethylethyl.

Preferably $R^7$ is hydrogen, methyl, ethyl, propyl, isopropyl, butyl, iso or tert-butyl, 2,2,2-trimethylethyl, methoxy, ethoxy, phenyl, benzyl or the same substituted by at least a halo group such as trifluoromethyl, chlorophenyl.

Preferably $R^8$ is hydrogen, methyl, ethyl, propyl, isopropyl, butyl, iso or ter-butyl, 2,2,2-trimethylethyl, phenyl, benzyl or the same substituted by at least a halo group such as trifluoromethyl, chlorobenzyl or where X is —CN.

Unless otherwise stated, references herein to the compounds of general formula (A) either individually or collectively are intended to include geometrical isomers i.e. both Z (Zusammen) and E (Entgegen) isomers and mixtures thereof (racemates).

With respect to the asymmetric hydrogenation process described below, the best results have been obtained for the Z (Zusammen) and E (Entgegen) isomers of the compounds of formula (A) where $R^1$ is methyl, $R^2$ and $R^4$ are H and X is —CONH$_2$ or —COOMe or —COOEt or —COOH. Within this group, compounds wherein $R^3$ is hydrogen, alkyl (especially propyl) or haloalkenyl (especially difluorovinyl) are particularly well suited.

An aspect of the invention concerns a process for preparing the compound having a general formula (A). This process includes the following reactions:

Compounds having a general formula (A), where X is —CONR$^5$R$^6$ or —COOR$^7$ or —CO—R$^8$ or CN, may conveniently be made by reaction of an α-ketocarboxylic acid derivative of general formula (C) where $R^1$ and X are described above, with a pyrrolidinone of general formula (D) where $R^2$, $R^3$, $R^4$ are described above, according to the following scheme (1).

Scheme (1)

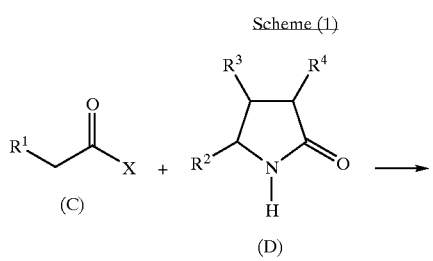

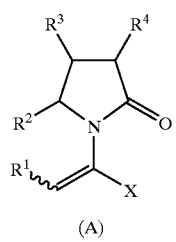

(A)

Compounds having a general formula (A) where X is —COOR$^7$ may conveniently be made by reaction of an α-ketocarboxylic acid derivative of general formula (C') where X is —COOR$^7$ with a pyrrolidinone of general formula (D) according to the following scheme (2).

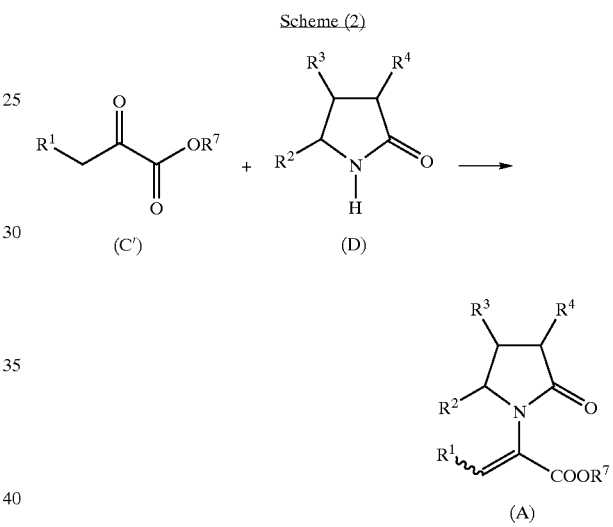

Suitable reaction conditions involve use of toluene under reflux. In the resulting compound (A), $R^7$ may readily be converted from H to alkyl or from allyl to H.

Derivatives of general formula (C) or (C') and pyrrolidones of general formula (D) are well known by the man of the art and can be prepared according to syntheses referred to in the literature, such as In "Handbook of Heterocyclic Chemistry" by A. Katrisky, Pergamon, 1985 (Chapter 4,) and in "Comprehensive Heterocyclic Chemistry" by A. Katrisky & C. W. Rees, Pergamon, 1984 (Volume 4, Chapters 3.03 & 3.06).

Compounds of general formula (A) where X is —CONH$_2$ or —CONR$^5$R$^6$ may conveniently be prepared by conversion of the corresponding acid (compound of formula (A) where X is CO$_2$H) to the acid chloride with subsequent ammonolysis or reaction with a primary or secondary amine of the general formula HNR$^5$R$^6$. The following two schemes (3 and 4) describe such a process.

Scheme (3)

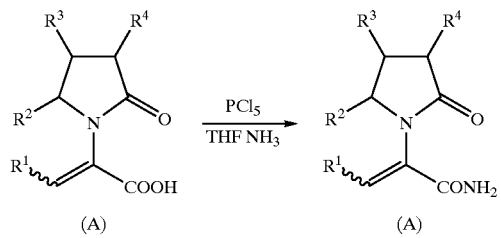

Scheme (4)

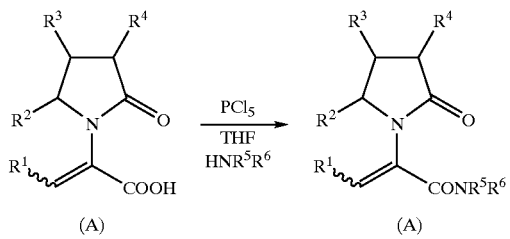

These reactions are preferably performed using PCl₅ to give an acid chloride followed by anhydrous ammonia or primary or secondary amine of the formula HNR⁵R⁶ to give the desired enamide amide.

Compounds of general formula (A) where X is —COOR⁷ may conveniently be made by conversion of the corresponding acid (compound (A) where X is COOH) obtained by Scheme (2) to the acid chloride with subsequent alcoholysis with the compound of formula R⁷—OH (alcohol) where R⁷ is defined above. (see Scheme 5)

Scheme (5)

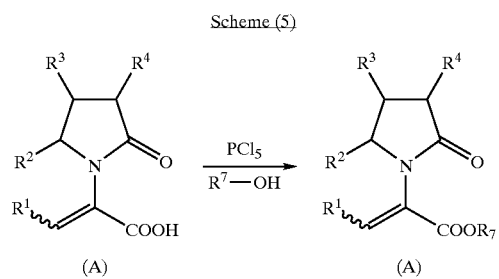

These reactions are preferably performed using PCl₅ to give an acid chloride followed by alcoholysis with R⁷—OH to give the desired ester.

The conditions of the above reactions are well known by the man skilled in the art.

In another aspect the invention concerns the use of compounds of formula (A) as synthesis intermediates.

The compound of formula (A) where X is —CONH₂ is of particular interest, as catalytic hydrogenation of this compound leads directly to Levetiracetam. Both the Z (Zusammen) and E (Entgegen) isomers of these compounds have been shown to undergo rapid and selective asymmetric hydrogenation to either enantiomer of the desired product. The representation of the bond joining the group R¹ to the molecule denotes either a Z isomer or an E isomer As a particular, example, the use of compounds (A) for the synthesis of compounds (B) may be illustrated according to the following scheme (6).

Scheme (6)

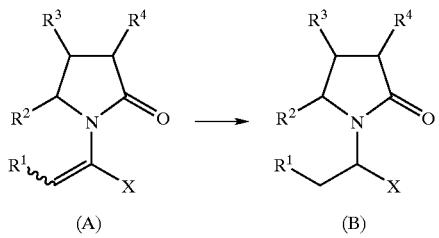

wherein R¹, R², R³, R⁴ and X are as noted above.

Preferably, R¹ is methyl, ethyl, propyl, isopropyl, butyl, or isobutyl; most preferably methyl, ethyl or n-propyl.

Preferably, R² and R⁴ are independently hydrogen or halogen or methyl, ethyl, propyl, isopropyl, butyl, isobutyl; and, most preferably, are each hydrogen.

Preferably, R³ is C1–5 alkyl, C2–5 alkenyl, C2–C5 alkynyl, cyclopropyl, azido, each optionally substituded by one or more halogen, cyano, thiocyano, azido, alkylthio, cyclopropyl, acyl and/or phenyl: phenyl phenylsulfonyl; phenylsulfonyloxy, tetrazole, thiazole, thienyl furryl, pyrrole, pyridine, whereby any phenyl moiety may be substituted by one or more halogen, alkyl, haloalkyl, alkoxy, nitro, amino, and/or phenyl; most preferably methyl, ethyl, propyl, isopropyl, butyl, or isobutyl.

Preferably, X is —COOH or —COOMe or —COOEt or —CONH₂; most preferably —CONH₂.

The compounds of formula (B) may be isolated in free form or converted into their pharmaceutically acceptable salts, or vice versa, in conventional manner.

Preferred individual compounds among the compounds having the general formula (B) have the formulas (B'), (B") and (B'").

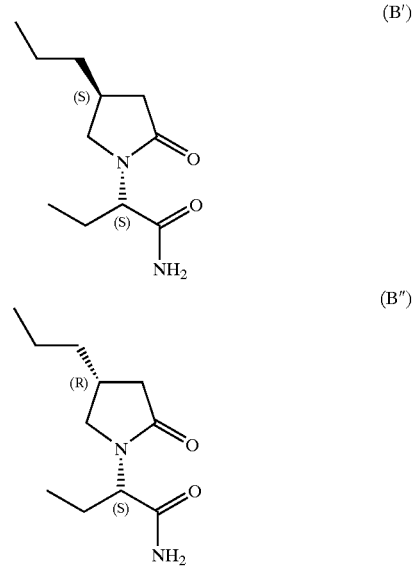

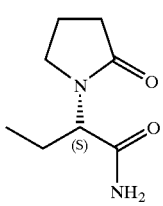
(B''')

The compounds of formula (B) are suitable for use in the treatment of epilepsy and related ailments. According to another embodiment, the invention therefore concerns a process for preparing a compound having a formula (B)

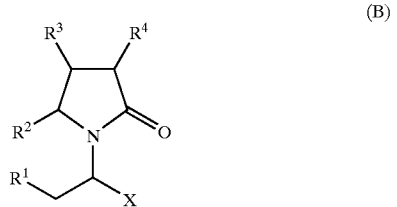
(B)

wherein $R^1$, $R^2$, $R^3$, $R^4$ and X are as noted above, via catalytic assymetric hydrogenation of the corresponding compound having the formula (A) as illustrated and defined above. Catalytic hydrogenation is described in many publications or books such as "Synthése et catalyse asymétriques—auxiliaries et ligands chiraux" Jacqueline Seyden-Penne (1994)—Savoirs actuel, interEdition/CNRS Edition—CH 7.1 "hydrogenation catalytique" page 287–300.

Unless otherwise stated, references herein to the compounds of general formula (B) either individually or collectively are intended to include geometrical isomers i.e. both Z (Zusammen) and E (Entgegen) isomers as well as enantiomers, diastereoisomers and mixtures of each of these (racemates).

Preferably, the process of the invention concerns the preparation of compounds of formula (B) in which $R^2$ and $R^4$ are hydrogen and X is —COOH or —COOMe or —COOEt or —CONH$_2$ and $R^1$ is methyl particularly those wherein $R^3$ is hydrogen, alkyl (especially propyl) or haloalkenyl (especially difluorovinyl). Best results have been obtained with the process for preparing levetiracetam, compound of formula (B) in which $R^1$ is methyl, $R^2$ and $R^4$ are hydrogen, $R^3$ hydrogen, propyl or difluorovinyl and X is —CONH$_2$.

Generally, this process comprises subjecting to catalytic hydrogenation a compound of formula (A) as described above. Preferably the compound of formula (A) is subjected to asymmetric hydrogenation using a chiral catalyst based on a rhodium (Rh) or ruthenium (Ru) chelate. Asymmetric hydrogenation methods are described in many publications or books such as "Asymmetric Synthesis" R. A Altken and S. N. Kilényi (1992—Blackie Academic & Professional or "Synthesis of Optically active-Amino Acids" Robert M. Willimas (1989)—Pergamon Press.

Rh(I)—, and Ru(II)—, complexes of chiral chelating ligands, generally diphosphines, have great success in the asymmetric hydrogenation of olefins. Many chiral bidentate ligands, such as diphosphinites, bis(aminophosphine) and aminophosphine phosphinites, or, chiral catalyst complexes, are described in the literature or are commercially available. The chiral catalyst may also be associated to a counterion and/or an olefin.

Although much information on the catalytic activity and stereoselectivity of the chiral catalysts has been accumulated, the choice of the ligands, the chiral catalysts and reaction conditions still has to be made empirically for each individual substrate. Generally the Rh(I) based systems are mostly used for the preparation of amino acid derivatives, while the Ru(II) catalysts give good to excellent results with a much broader group of olefinic substrates. Chiral catalyst chelators which may be used in the present invention, are DUPHOS, BPPM, BICP, BINAP, DIPAMP, SKEWPHOS, BPPFA, DIOP, NORPHOS, PROPHOS, PENNPHOS, QUPHOS, BPPMC, BPPFA. In addition to this, supported or otherwise immobilised catalysts prepared from the above chelators may also be used in the present invention in order to give either improved conversion or selectivity, in addition to improved catalyst recovery and recycling. Preferred chiral catalyst chelators for use in the method of this invention are selected from DUPHOS or Methyl, Diethyl, Diisopropyl-DUPHOS (1,2-bis-(2,5-dimethylphospholano)benzene—U.S. Pat. No. 5,171,892), DIPAMP (Phosphine, 1,2-ethanediylbis((2-methoxyphenyl) phenyl—U.S. Pat. No. 4,008,281 and No. 4,142,992), BPPM (1-Pyrrolidinecarboxylic acid. 4-(diphenylphosphino)-2-((diphenylphosphino)methyl)-, 1,1-dimethylethyl ester—Japanese patent N° 87045238) and BINAP (Phosphine, (1,1'-binaphthalene)-2,2'-diylbis (diphenyl—European patent No. 0 366 390).

The structures of these chelators are shown below.

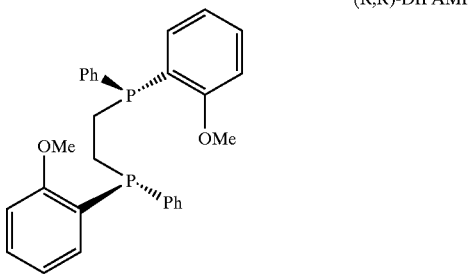
(R,R)-DIPAMP

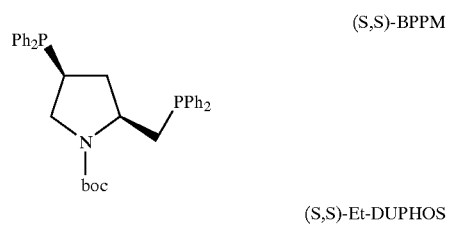
(S,S)-BPPM

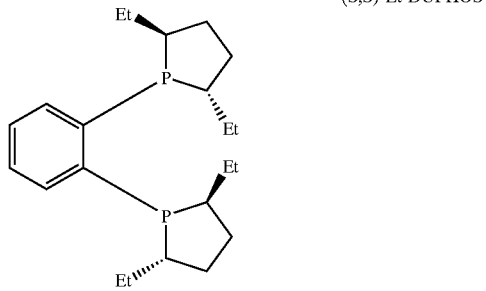
(S,S)-Et-DUPHOS

-continued

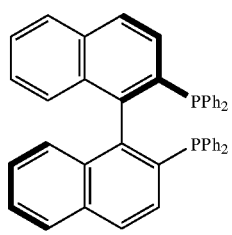
(R)-BINAP

Preferred solvents for use in the method of this invention are selected from, tetrahydrofuran (THF), dimethylformamide (DMF), ethanol, methanol, dichloromethane (DCM), isopropanol (IPA), toluene, ethyl acetate (AcOEt).

The counterion is selected from halide (halogen(−)), $BPh_4$ (−) $ClO_4$(−). $BF_4$(−), $PF_6$(−), $PCl_6$(−), OAc(−), triflate (OTf (−)), mesylate or tosylate. Preferred counterions for use with these chiral catalysts are selected from OTf(−). BF4(−) or OAc(−).

The olefin is selected from ethylene, 1,3-butadiene, benzene, cyclohexadiene, norbornadiene or cycloocta-1,5-diene (COD).

Using these chiral catalysts, in combination with a range of counter-ions and at catalyst-substrate ratios ranging from 1:20 to 1:20,000 in a range of commercially available solvents it is possible to convert compounds of formula (A) into laevorotary or dextrorotary enantiomers of compounds of formula (B) having high % of enantiomeric excess (e.e.) and in excellent yield, and high purity. Moreover, this approach will use standard industrial plant and equipment and have cost advantages.

This asymmetric synthesis process will also be lower cost due to the avoidance of recycling or discarding the unwanted enantiomer obtained by a conventional synthesis process.

Best results have been obtained with the process for preparing (S)-α-ethyl-2-oxo-1-pyrrolidine acetamide or (R)-α-ethyl-2-oxo-1-pyrrolidine acetamide , wherein it comprises subjecting a compound of formula A' in the form of a Z isomer or an E isomer to asymmetric hydrogenation using a chiral catalyst according to the following scheme.

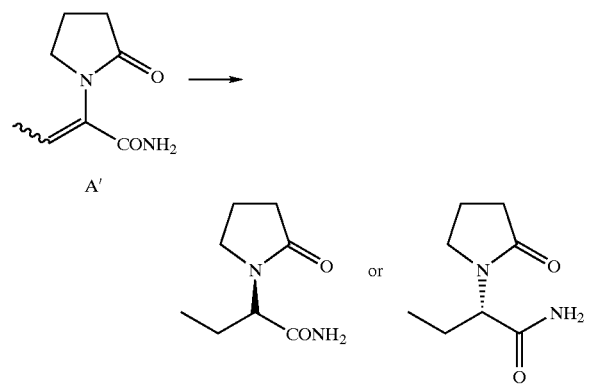

In what follows, reference is made particularly to four compounds of formula (A) in which $R^1$ is methyl, $R^2$, $R^3$ and $R^4$ are hydrogen and, for the compound hereinafter identified as precursor A1, X is —COOH;

for the compound hereinafter identified as precursor A2, X is —COOMe;

for the compound hereinafter identified as precursor A2', X is —COOEt; and for the compound hereinafter identified as precursor A3, X is —$CONH_2$.

As will be appreciated by the skilled person, depending on the substitution pattern, not all compounds of general formula (A) and (B) will be capable of forming salts so that reference to "pharmaceutically acceptable salts" applies only to such compounds of general formulae (A) or (B) having this capability.

The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

EXAMPLE 1

The preparation of precursor A1 was carried out in 70% crude yield by reacting α-ketobutyric acid and pyrrolidinone in refluxing toluene, see Scheme 7. By Z:E, we mean the ratio of Z isomer amount on E isomer amount.

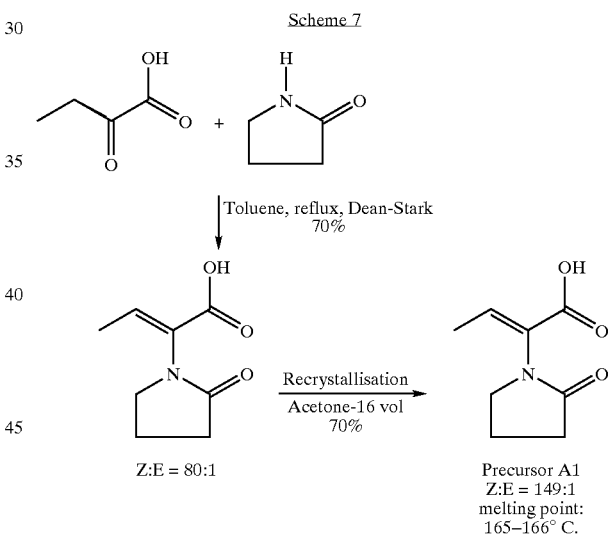

Scheme 7

Precursor A1
Z:E = 149:1
melting point: 165–166° C.

The crude product was recrystallised from acetone in 70% yield. The geometry of the double bond was assigned to be Z on the basis of correlation with the $^1$H-NMR (Nuclear Magnetic Resonance) spectral data for known compounds with similar structure.

EXAMPLE 2

Precursor $A_2'$ was prepared from A1 with diazomethane in THF. It was observed that the Z-E ratio changes from 80:1 to 29:1 during distillation (see Scheme 8).

Scheme 8

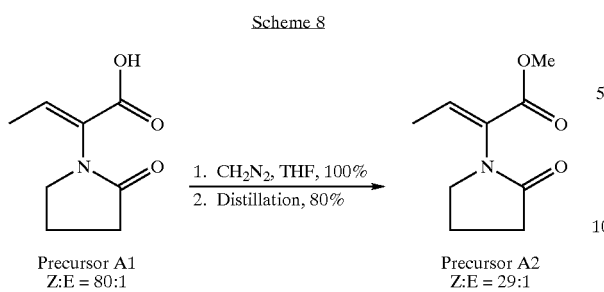

Precursor A1
Z:E = 80:1

1. CH$_2$N$_2$, THF, 100%
2. Distillation, 80%

Precursor A2
Z:E = 29:1

The E-isomer of precursor A$_2$' has been obtained as shown in Scheme 9 from Z-isomer of precursor A$_1$ with ethanol, dicyclohexylcarbodiimide (DCC) and dimethylaminopyridine (DMAP).

Scheme 9

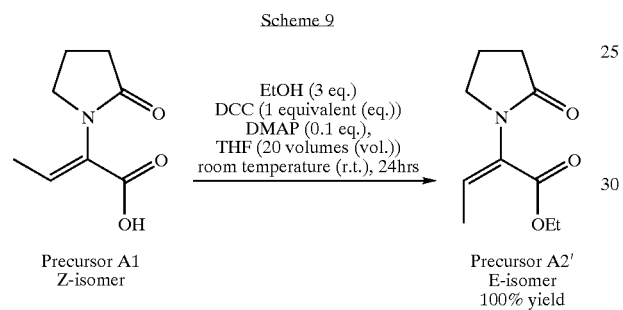

Precursor A1
Z-isomer

EtOH (3 eq.)
DCC (1 equivalent (eq.))
DMAP (0.1 eq.),
THF (20 volumes (vol.))
room temperature (r.t.), 24hrs Precursor A2'
E-isomer
100% yield Esterification of precursor A1 was also carried out on a small scale with PCl$_5$ in THF then MeOH and gave exclusively the desired methyl esters (E:Z=5:1), see Scheme 10.

Scheme 10

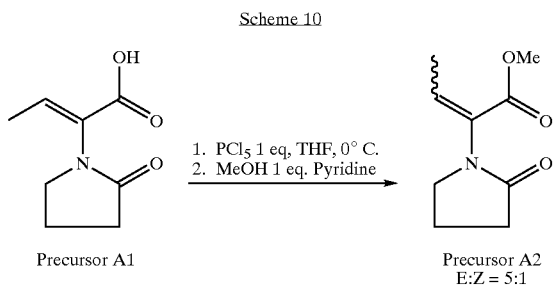

Precursor A1

1. PCl$_5$ 1 eq, THF, 0° C.
2. MeOH 1 eq. Pyridine

Precursor A2
E:Z = 5:1

EXAMPLE 3

Precursor A2 was also prepared by reacting ketobutyric acid methyl ester and pyrrolidinone in refluxing toluene in the presence of a catalytic amount of POCl$_3$, see Scheme 11.

Scheme 11

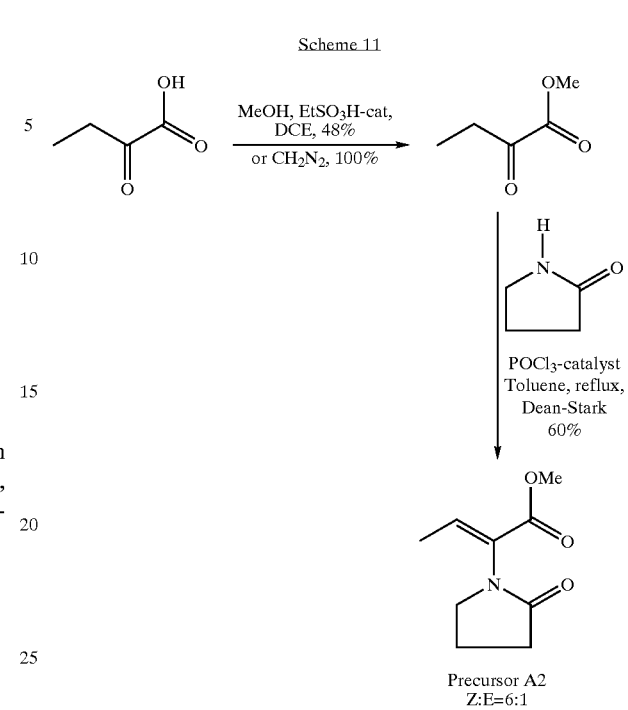

MeOH, EtSO$_3$H-cat, DCE, 48%
or CH$_2$N$_2$, 100%

POCl$_3$-catalyst
Toluene, reflux,
Dean-Stark
60%

Precursor A2
Z:E=6:1

The esterification of the ketobutyric acid was carried out either with methanol following a literature method, or with diazomethane. The subsequent condensation reaction gave precursor A2 in 60% yield. This method leads to a higher content of E-isomer in comparison to the route via precursor A1 (Scheme 8). Both routes allow for the preparation of other ester derivatives of precursor A2.

EXAMPLE 4

Synthesis of the precursor A3 has been effected by reacting the enamide acid with PCl$_5$ to give the acid chloride and then with gaseous ammonia to obtain the desired enamide amide A3. The product has been confirmed as the Z-isomer.

The crude enamide amide A3 was isolated from the reaction mixture by dissolving it in THF-MeOH and filtering to remove inorganic residues. After evaporation of the solvent a yellow solid was obtained. The crude material was purified by dry flash chromatography followed by recrystallisation from i-PrOH to afford pure material. This procedure has been successfully applied to produce a single batch of A3 (118 g, 54%, >99% by peak area) and is outlined in Scheme 12.

Scheme 12

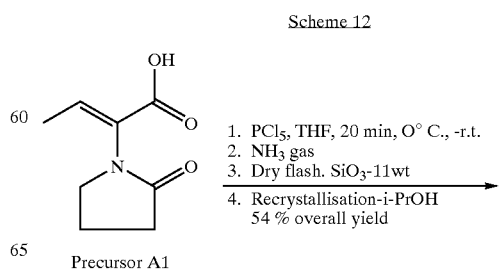

Precursor A1

1. PCl$_5$, THF, 20 min, 0° C., -r.t.
2. NH$_3$ gas
3. Dry flash. SiO$_3$-11wt
4. Recrystallisation-i-PrOH
54 % overall yield

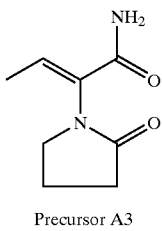

Precursor A3

In most cases of the asymmetric hydrogenation of precursors, the catalyst has been prepared in situ by reacting [Rh(COD)$_2$]$^+$OTf$^-$ and the respective chiral ligand in the solvent of choice followed by addition of substrate. Some catalysts are commercially available and these have been used without further purification.

EXAMPLE 5

Results from the asymmetric hydrogenation of precursors A1 and A2 using a number of rhodium based catalyst systems are summarised in the following Table 1. These reactions have been performed with between 0.005 mol % and 5 mol % of catalyst and 100 mg or 200 mg of substrate at ambient temperature (room temperature: rt) for 24 hours.

Reaction conditions such as the H$_2$ pressure, the kind of solvents, the amount of precursor have been modified in order to obtain the optimal conditions. All products have been isolated by evaporation of the solvent from the reaction mixture and analysed without further purification by $^1$H-NMR spectroscopy.

The HPLC (High Performance Liquid Chromatography) method for % e.e, determination of the hydrogenation product of precursor A1 proved difficult to develop. Therefore, we converted the crude products into their methyl esters using diazomethane in THF solution. The ester derivatives were then analysed using a chiral HPLC method for monitoring the hydrogenation of enamide ester A2. For the HPLC method, we used a Chiracel OD 4.6×250 mm column and IPA/n-hexane (95:05) as eluant.

For the hydrogenated product of precursor A2, the e.e, results have been obtained by the following chiral HPLC method: Chiralcel OD 4.6×250 mm, IPA-Hexane (5:95 v/v), 205 nm, 1 ml/min at ambient temperature (rt), sample 1 mg/ml, 13 min (S-enantiomer), 16 min (R-enantiomer). Initially, the screening was carried out on 100 mg scale with 5 mol % of catalyst.

The results in % of enantiomeric excess (e.e.) are positive to express the percentage of laevorotatory S-enantiomer and negative to express the percentage of dextrorotatory R-enantiomer.

TABLE 1

| St. Ma. | Am. Mg | Catalyst | Cou. | Loa. | Solv. | H2 Pres. | C.V. % | e.e. % |
|---|---|---|---|---|---|---|---|---|
| A1 | 100 | (S,S)-Et-DUPHOS | OTf(−) | 5.0 | EtOH | 4 | 100 | 95 |
| A1 | 100 | (S,S)-BPPM | OTf(−) | 5.0 | EtOH | 1 | 68 | −64 |
| A1 | 100 | (R,R)-DIPAMP | BF4(−) | 5.0 | DCM | 4 | 100 | 92 |
| A2 (Z) | 200 | (S,S)-Et-DUPHOS | OTf(−) | 2.0 | EtOH | 4 | 100 | 98.8 |
| A2 (Z) | 200 | (S,S)-Et-DUPHOS | OTf(−) | 0.5 | EtOH | 4 | 100 | 99.1 |
| A2 (Z) | 200 | (S,S)-Me-DUPHOS | OTf(−) | 1.0 | EtOH | 5 | 100 | 98.9 |
| A2 (Z) | 300 | (S,S)-Me-DUPHOS | OTf(−) | 2.0 | IPA | 5 | 100 | 97.9 |
| A2' (E) | 200 | (S,S)-Me-DUPHOS | OTf(−) | 0.5 | EtOH | 5 | 100 | 99.4 |
| A2' (E) | 300 | (S,S)-Me-DUPHOS | OTf(−) | 0.5 | IPA | 5 | 100 | 94.0 |
| A2 (E) | 4000 | (S,S)-Me-DUPHOS | BF4(−) | 0.025 | MeOH | 5 | 100 | 97.4 |
| A2 (Z) | 4000 | (S,S)-Me-DUPHOS | BF4(−) | 0.01 | MeOH | 5 | 99 | 99 |
| A2 (Z) | 4000 | (S,S)-Me-DUPHOS | BF4(−) | 0.005 | MeOH | 5 | 25 | 97 |
| A2' (E) | 300 | (S,S)-BPPM | OTf(−) | 0.5 | MeOH | 1 | 100 | −99.3 |
| A2' (E) | 300 | (S,S)-BPPM | OTf(−) | 0.5 | EtOAc | 1 | 100 | −95.2 |
| A2 (E) | 300 | (S,S)-BPPM | OTf(−) | 0.5 | Toluene | 1 | 100 | −96.2 |
| A2 (Z) | 200 | (R,R)-DIPAMP | BF4(−) | 2.0 | EtOAc | 5 | 100 | 94.5 |
| A2' (E) | 200 | (R,R)-DIPAMP | BF4(−) | 0.5 | EtOAc | 5 | 92 | 96.5 |

In this table, St. Ma. represents Starting material; Am. represents Amount; Cou. represents Counterion; Loa. represents Loading Mol %; Solv. represents Solvent, H2 Pres. represents H2 pressure (atm); and C.V. represents Conversion.

EXAMPLE 6

Asymmetric Hydrogenation of Precursor A3

Using the same approach as in example 5; a number of rhodium and ruthenium catalysts have been screened, see Scheme 13 and Table 2 for representative results.

TABLE 2

| Amount A3 mg | Catalyst | metal | Cou. | Loa. mol % | solvent | volume | H$_2$ Pres. atm | Reaction time hours | Reaction temp. | Conversion % | e.e. % |
|---|---|---|---|---|---|---|---|---|---|---|---|
| 100 | (R)-BINAP | Ru | OAc(−) | 2.5 | EtOH | 25 | 4.5 | 16 | rt | 100 | −82.7 |
| 500 | (R)-BINAP | Ru | OAc(−) | 1.0 | EtOH/H$_2$O 5:1 | 20 | 4 | 16 | rt | 100 | −85 |

TABLE 2-continued

| Amount A3 mg | Catalyst | metal | Cou. | Loa. mol % | solvent | volume | H₂ Pres. atm | Reaction time hours | Reaction temp. | Conversion % | e.e. % |
|---|---|---|---|---|---|---|---|---|---|---|---|
| 500 | (R,R)-DIPAMP | Rh | BF4(-) | 0.5 | DCM | 20 | 4 | 18 | rt | 80–90 | 90 |
| 500 | (R,R)-DIPAMP | Rh | BF4(-) | 1.0 | DCM | 20 | 4 | 18 | rt | 100 | 93 |
| 500 | (R,R)-DIPAMP | Rh | BF4(-) | 2.5 | DCM | 20 | 4 | 70 | rt | 100 | 94.4 |
| 500 | (R,R)-DIPAMP | Rh | BF4(-) | 2.5 | EtOH | 20 | 4 | 70 | rt | 100 | 93.8 |
| 500 | (R,R)-DIPAMP | Rh | BF4(-) | 1.0 | EtOH | 20 | 4 | 16 | rt | 100 | 85 |
| 2000 | (S,S)-BPPM | Rh | OTf(-) | 0.5 | EtOH | 10 | 1 | 40 | 65–70° C. | 100 | -7 |
| 500 | (S,S)-Et-DUPHOS | Rh | OTf(-) | 0.5 | DCM | 40 | 4 | 16 | rt | 100 | 97 |
| 500 | (S,S)-Et-DUPHOS | Rh | OTf(-) | 2.5 | DCM | 40 | 4 | 17 | rt | 100 | 97 |

In this table, Cou. represents Counterion; Loa. represents Loading Mol %; H2 Pres. represents H2 pressure; and rt represents room temperature.

As above, the rhodium catalysts have been prepared in situ or purchased arid used without further purifications. The ruthenium catalysts were prepared according to known literature procedures. Most experiments have been conducted on a 100 mg to 15 g scale with between 0.001 mol % and 5 mol % of catalyst. The crude products have been analysed by $^1$H. $^{13}$C NMR spectroscopy and by chiral HPLC analysis.

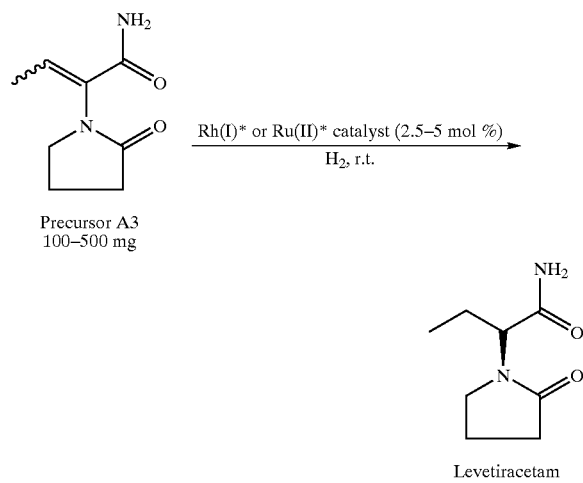

Scheme 13

Precursor A3
100–500 mg

Rh(I)* or Ru(II)* catalyst (2.5–5 mol %)
H₂, r.t.

Levetiracetam

EXAMPLE 7

Asymmetric Hydrogenation of Precursor A3 with Rh-(Et,Et)-DUPHOS

The results of the hydrogenation of A3 with Rh-DUPHOS catalyst are shown in Table 3. These reactions have been performed in the same way as in example 5 and 6, with a hydrogen pressure of 4 atmospheres.

Usually, enantioselectivities in the Rh-DUPHOS catalysed hydrogenations of α-acylaminoacrylic acid derivatives show very little solvent effect. However, it remains impossible to predict a priori what the effect of the solvent would be on the enantioselectivity and the rate of the reaction for a given substrate. It has been observed that the hydrogenation of A3 is highly solvent dependent, The non-coordinating, aprotic solvent DCM was found superior. Hydrogenations in protic alcoholic solvents resulted in slower reactions and reduced selectivity. Similarly, reduced conversions were observed in polar aprotic solvents such as EtOAc and THF, both of which may be expected to coordinate to the metal and inhibit catalysis. The inhibition by coordinating solvents probably suggests that A3 is a poorly coordinating substrate, especially in comparison to other α-acylaminoacrylic acid derivatives.

Nevertheless, excellent results have been obtained in DCM. As can be seen, enantioselectivities of 97 to 98% e.e, were consistently achieved on 0.5 to 15 g scale in this solvent. Other promising results were obtained in EtOAc-DCM solvent mixture and in toluene.

TABLE 3

Hydrogenation of A3 with [Rh-COD-(S,S)-Et DUPHOS]OTf

| Amount A3 mg | Catalyst mol % | solvent | solvent volume | Reaction time (hours) | C.V. % | e.e. % |
|---|---|---|---|---|---|---|
| 500 | 1.0 | AcOEt/DCM 5:1 | 30 | 17 | 95 | 96 |
| 500 | 1.0 | DCM | 20 | 17 | 100 | 97 |
| 500 | 0.5 | DCM | 30 | 16 | 99 | 98 |
| 500 | 0.5 | DCM | 40 | 16 | 100 | 97 |
| 500 | 2.5 | DCM | 40 | 17 | 100 | 97 |
| 10000 | 1.0 | Toluene | 30 | 65 | 93 | 92 |
| 500 | 1.0 | Toluene | 30 | 16 | 95 | 95 |

In this table C.V. represents Conversion.

A. Preparation of Precursor A1: (Z)-2-(2-oxotetrahydro-1H-1-pyrrolyl)-2-butenoic acid (Precursor A1)

A 1 l flask fitted with a magnetic stirring bar and a Dean-Stark trap was charged with 2-oxobutanoic acid (25 g, 245 mmol), toluene (500 ml, 20 vol) and 2-pyrrolidinone (37.2 ml, 490 mmol, 2 equiv). The reaction mixture was stirred under reflux with azeotropic removal of water via the Dean-Stark trap for 5.5 hours. The solution was then concentrated to ca, 90 ml (3.6 vol) and allowed to cool slowly to ambient temperature. Off-white solid started to come out of solution at around 55° C. The solid was filtered, the cake was washed with toluene (2×1 vol) followed by dichloromethane (3×1 vol) and dried on the filter under vacuum for 5 min to afford crude material (28 g, 70% yield). The crude product was dissolved in acetone (450 ml, 16 vol) at reflux, cooled slowly to ambient temperature and allowed to crystallise over 12 hrs at −15 to −20° C. Pure product was obtained as a white crystalline solid (21 g, 51% overall yield).

Melting point (m.p.), 165.5–166° C. $^1$H NMR (CDCl$_3$): δ (chemical shift) 2.13 (5H, doublet (d) and multiplet), 2.51 (2H, triplet (t)), 3.61(2H, t), 6.27(1H, quadruplet (q)), 8 to 10(1H, broad); signals for E-isomer, δ 1.85(3H, t), 7.18(1H, q). $^{13}$C NMR(MeOH-d4): δ 14.7, 19.6, 32.1, 51.4, 130.8, 137.7, 166.6, 177.9. Z:E ratio 149:1, by $^1$H NMR.

Thin Layer Chromatography (TLC): SiO$_2$, Toluene/AcOH/MeOH (4:1:0.5). UV and anisaldehyde stain.

B. Preparation of Precursor A2: Methyl (Z)-2-(2-oxotetrahydro-1H-1-pyrrolyl)-2-butenoate (Precursor A2)

Precursor A1 (12 g, 71 mmol) was dissolved in THF (240 ml, 20 vol) at 0–5° C. A solution of diazomethane in ether (200 ml, ~78 mmol, 1,1 equiv) was added portionwise to the reaction mixture, keeping the temperature below 5° C. The reaction mixture turned yellow colour with the last portion of the reagent. This was stirred for additional 30 min at low temperature and then allowed to warm up. The remaining traces of diazomethane were destroyed by dropwise addition of very dilute acetic acid in THF until the yellow solution became colourless. The reaction mixture was concentrated in vacuo and the crude material was distilled (93–94° C., 0.01 mm Hg) to afford pure product (9.44 g, 73%) as a colourless oil. which solidifies on cooling below 10° C.

$^1$H NMR (CDCl$_3$): δ 2.0(3H, d), 2.1(2H, m), 2.43(2H, t), 3.54(2H, t), 3.76(3H, s), 5.96(1H, q); signals for E-isomer, δ 1.75(3H, d) and 7.05(1H, q). $^{13}$C NMR(MeOH-d4): δ 14.4, 19.7, 32, 51, 52.6, 130.1, 134.4, 165.6, 177.4. Z:E ratio 29:1 by $^1$H NMR.

C. Preparation of Methyl 2-oxobutanoate.

2-Oxobutanoic acid (15 g) was distilled under reduced pressure using a Kugelruhr apparatus (84° C., 20 mm Hg) to yield 14 g of purified material. Distilled 2-oxobutanoic acid (14 g) was dissolved in methanol (anhydrous, 20 ml, 1.4 vol) and dichloroethane (anhydrous, 80 ml, 5.7 vol) in the presence of a few drops of ethanesulfonic acid. The reaction mixture was stirred at reflux for 18 hrs under an inert atmosphere. Then it was allowed to cool down, dried over MgSO$_4$, filtered and concentrated in vacuo. The crude was purified by distillation (b.p, 76° C., 20 mm Hg) to give a pure product as a colourless oil (7.53 g, 48% yield).

$^1$H NMR (CDCl$_3$): δ 0.88(3H, t), 2.66(2H, q), 3.63(3H, s) ref. Biochemistry, 2670, 1971, D. Preparation of Methyl (Z)-2-(2-oxotetrahydro-1H-1-pyrrolyl)-2-butenoate (Precursor A2)

A 100 ml flask fitted with a magnetic stirring bar and a Dean-Stark trap was charged with methyl 2-oxobutanoate (7.5 g, 73 mmol), toluene (50 ml, 7 vol) and 2-pyrrolidinone (8.4 ml, 111 mmol, 1.5 equiv) followed by dropwise addition of POCl$_3$ (1.6 ml, 20 mmol. 0.27 equiv). The reaction mixture was stirred under reflux with azeotropic removal of water via the Dean-Stark trap for 8 hours. After cooling down the solution was washed with 10% aq KHSO$_4$ (2×3 vol). The aqueous phase was saturated with NaCl and back extracted with toluene (1×6 vol). The combined organic phase was dried over MgSO$_4$, filtered and concentrated in vacuo to afford crude material (7.5 g) as an orange mobile oil. The crude oil was distilled (92–94° C., 0. 1 mm Hg) and gave pure product (4.7 g, 60%) as a colourless oil.

Z:E ratio 6:1 by $^1$H NMR.

E. Preparation of Methyl (E)-2-(2-oxotetrahydro-1H-1-pyrrolyl)-2-butenoate (Precursor A2)

A dry 100 ml flask fitted with a magnetic stirrer bar was charged with Z-A1 (2 g, 11.8 mmol), ethanol (2,2 ml, 37.3 mmol), tetrahydrofuran (THF, 40 ml, 20 vol) and dimethylaminopyridine (DMAP, 150 mg, 1,23 mmol) under an nitrogen atmosphere. The reaction mixture was cooled to 0° C. before adding dicyclohexylcarbodiimide (DCC, 2.46 g, 11.9 mmol), then heated to ambient temperature. The reaction mixture was stirred vigorously 21 hours. After that hexane (40 ml) was added to precipitate a solid. The precipitate was filtered off and the filtrate was concentrated in vacuo to afford 3.03 g of colourless liquid oil. The oil in water (40 ml) was washed with dichloromethane (DCM, 40 ml then 2×20 ml), the solvent was dried by Na$_2$SO$_4$ and concentrated in vacuo to afford 2 g of E-A2 ethyl ester (100% yield).

F. Preparation of Precursor A3 (Z)-2-(2-oxotetrahydro-1H-1-pyrrolyl)-2-butenenamide (Precursor A3).

A 20-liter flange flask was set up for stirring under inert atmosphere and was charged with A1 (222 g, 1.313 mol, 1 wt) and anhydrous THF (7.0 liter., 30 vol). The reaction mixture was allowed to cool below 5° C. and PCl$_5$ (300 g, 1.44 mol, 1.1 equiv) was added portionwise keeping the reaction temperature below 10° C. The reaction mixture was stirred at −5 to 0° C. for one hour, allowed to warn up to 15° C. to dissolve the remaining PCl$_5$, and then cooled back below 0° C. A condenser filled with dry ice/acetone was fitted and ammonia gas (~200 g) was bubbled slowly through the solution, keeping temperature below 15° C. The suspension was stirred for an additional 15 min and the excess ammonia was removed by bubbling nitrogen gas through for several minutes. Methanol (3.7 liter, 17 vol) was added, the reaction mixture was refluxed for 1.5 hrs, then cooled below 30° C., filtered, and washed with THF/MeOH (2:1, 600 ml, ~3 vol). The filtrate was evaporated to give a yellow solid. This material was dissolved in methanol (640 ml, ~3 vol) and ethyl acetate (440 ml, 2 vol) and purified using dry-flash chromatography (SiO$_2$, 11 wt, 3.4 Kg) with EtOAc/MeOH (6:1) to afford crude product (288 g). The crude product was recrystallised from isopropanol (1.9 liters, ~8.5 vol) to give white crystals (127 g). Me solid was dried in vacuum oven at ambient temperature for 2 days to yield A3 (118 g, 54%).

$^1$HNMR (CDCl$_3$+few drops MeOD): δ 6.75 (1H,q) 3.5 (2H,t) 2.5 (2H,t) 2.15 (2H,m) 1.7 (3H,d), traces of impurities.

Elemental analysis (% m/m): C, 56.90 (57.13% theory); H, 7.19 (7.19% theory); N, 16.32 (16.66% theory).

A3 (108 g) was recrystallised again from IPA (1 L, 9.3 vol) to afford a final batch used in the hydrogenation studies (100 g, 93%). m.p, 172.0° C.–174.2° C.

Elemental analysis (% m/m): C, 56.95 (57.13% theory); H, 7.10 (7.19% theory); N, 16.38. (16.660% theory).

TLC: SiO$_2$, Toluene/AcOH/MeOH (4:1:0.5). UV and anisaldehyde stain.

G. Preparation of Chiral Rhodium and Ruthenium Catalysts—Preparation of [Rh(I)L*COD]$^{+OTf-}$ (0.15 M solutions)

[Rh(I)COD$_2$]$^+$ OTf$^-$ (35 mg, 0.075 mmol) and a chiral ligand (L*, 0.083 mmol, 1. 1 equiv) were weighed quickly in air and charged to a flask. The flask was sealed with a rubber septum and purged with argon. Anhydrous, degassed solvent (5 ml, 143 vol) was added via the septum. The reaction mixture was degassed (3× vacuum/argon) and stirred for 30 min or until all solids had dissolved.

H. Preparation of Rh(I)(MeOH)$_2$[(R)-Binap]

A dry 200 ml Schlenk tube fitted with a magnetic stirrer bar was charged with [Rh(I)(nbd)$_2$]ClO$_4$ (251 mg, 0.649 mmol) and (R)-Binap (405 mg, 0.65 mmol) under an argon atmosphere. Dichloromethane (anhydrous, degassed, 5 ml, 20 vol) was added via a syringe and the reaction mixture was degassed (3× vacuum/argon). Tetrahydrofuran (anhydrous, degassed, 10 ml, 40 vol) was added slowly followed by hexane (anhydrous, degassed, 20 ml. 80 vol) The resulting suspension was kept at 0–5° C. for 16 hrs. The solvents were decanted under argon and methanol (anhydrous, degassed, 5 ml, 20 vol) was added. The Schlenk tube was purged with hydrogen (5× vacuum/hydrogen) and stirred at ambient temperature for 1.5 hrs. The clear red orange solution was transferred to another Schlenk tube (purged with argon) via a syringe. The catalyst solution was stored under argon at 0–5° C. and used directly for hydrogenation (Tetrahedron, 1245, 1984).

I. Preparation of [RuCl(R)-Binap)(C$_6$H$_6$)]$^{+Cl-}$

A dry 200 ml Schlenk tube fitted with a magnetic stirrer bar was charged with [RuCl$_2$(C$_6$H$_6$)]$_2$ (0.33 g, 0.66 mmol) and (R)-Binap (0.815 g, 1.3 mmol) under argon atmosphere. Degassed anhydrous benzene (90 ml, 60 vol) and ethanol (130 ml, 330 vol) were added and the solution was degassed (3× vacuum/argon). The red brown suspension was heated to 50–55° C. for 45 min giving a clear brown solution. This was filtered through a celite pad under argon into another Schlenk tube. The solvents were evaporated in vacuo to afford the catalyst as a yellow orange solid (1.08 g, 86%) which was stored under argon at 0–5° C. (J.Org.Chem., 3064, 19941).

J. Preparation of [RuCl(R)-Binap)(C$_6$H6)]$^{+BF_4-}$

A dry 100 ml Schlenk tube fitted with a magnetic stirrer bar was charged with [RuCl(R)-Binap)(C$_6$H$_6$)]+Cl− (0.45 g, 0.52 mmol) and degassed anhydrous dichloromethane (20 ml, 44 vol) under argon atmosphere. The resulting solution was degassed (3× vacuum/argon) and transferred via a syringe to another Schlenk tube containing a degassed suspension of AgBF$_4$ (0.15 g, 0.77 mmol, 1.5 equiv) in dichloromethane (10 ml, 22 vol). Tile mixture was stirred vigorously for 0.5 h and then filtered through a celite pad under argon atmosphere. The filtrate was concentrated in vacuo to give the catalyst as a green solid (0.42 g, 88%) which was stored under argon at 0–5° C. (J.Org.Chem., 3064, 1994).

K. Preparation of Ru(OCOCH$_3$)$_2$[(R)-Binap]

A dry 200 ml Schlenk tube fitted with a magnetic stirrer bar was charged with [RuCl$_2$(C$_6$H$_6$)]$_2$ (0.805 g, 1.60 mmol) and (R)-Binap (1.89 g, 3.03 mmol, 0.95 equiv) under an argon atmosphere. Anhydrous, degassed dimethylformamide (30 ml, 38 vol) was added and the solution was degassed (3× vacuum/argon). The reaction mixture was heated to 100° C. for 10 min to give a dark red solution which was then cooled to ambient temperature. A degassed solution of sodium acetate (5.2 g, 63.4 mmol, 20 equiv) in methanol (50 ml, 60 vol) was charged to the reaction vessel and stirred for 5 min. Degassed water (50 ml, 60 vol) and toluene (25 ml, 30 vol) were added and the reaction mixture was stirred vigorously for 5 min. The toluene layer was transferred via a syringe to another dry Schlenk tube (purged with argon) and the aqueous phase was extracted with toluene (2×25 ml). The combined toluene solutions were washed with water (4×10 ml), the solvent was concentrated in vacuo at 45° C. and dried for 12 hrs under vacuum (0.1 mm Hg). The yellow brown solid was dissolved in toluene (25 ml) without stirring and hexane (75 ml) was added slowly to form a second layer on top. The two phase mixture was left to stand at ambient temperature for 7 hrs and then at 0–5° C. for 3 days. The catalyst crystallised out. The solvents were removed via a syringe under an argon atmosphere, the solid was washed with hexane (20 ml) and dried under vacuum for 2 hrs to give the catalyst as an yellow brown solid (1.76, 70%) which was stored under argon at 0–5° C. (J.Org. Chem., 4053, 1992).

L. Asymmetric Hydrogenation of Precursors A1, A2, A3.

The asymmetric hydrogenation follows the same protocol for each precursor. Therefore, only the asymmetric hydrogenation of A3 has been described below.

Asymmetric hydrogenation of precursors A3.

Hydrogenation at atmospheric pressure of H$_2$

A dry 100 ml Schlenk tube fitted with a magnetic stirrer bar was charged with the substrate (500 mg, 3 mmol) and purged with argon gas. Degassed solvent was added via a syringe followed by addition of a catalyst solution (0.5 to 2.5 mol %). The reaction injure was degassed (3× vacuum/ argon) and then purged with hydrogen (5× vacuum/ hydrogen) using hydrogen balloon. The reaction was stirred for 16–65 hrs at ambient temperature. The hydrogen atmosphere was exchanged with nitrogen and the solvent was evaporated in vacuo to afford a crude product, which was analysed by NMR spectroscopic analysis and chiral HPLC analysis.

Hydrogenation Occurred at a Pressure of 4 atm.

All manipulations were carried out in an AtmosBag™ (Aldrich Chemical Co.) under an argon atmosphere. The substrate (500–10000 mg,) was placed in stainless steel high pressure vessel (Vinci Technologies Ltd, France) fitted with a teflon beaker (or glass dish) and a teflon coated magnetic stirrer bar. Degassed solvent and a catalyst or a catalyst solution (0.25 to 2.5 mol %) was added. The vessel was sealed and purged with hydrogen by pressurising the vessel to 4.5–5.5 atm and then releasing the pressure (5 times). Finally, the pressure was adjusted to the desired level and the reaction mixture was stirred at ambient temperature for 16–65 hrs. Upon completion the hydrogen atmosphere was exchanged with nitrogen and the solvent was evaporated in vacuo to afford a crude product, which was analysed by NMR spectroscopic analysis and chiral HPLC analysis.

Purification of Final Material Purification of (S)-α-ethyl-2-oxo-1-pyrrolidine acetamide (Levetiracetam).

Levetiracetam obtained by asymmetric hydrogenation as described above (5 g, 98% e.e.) was dissolved in water (20 ml, 4 vol) and extracted with ethyl acetate (3×10 ml, 3×2 vol). The organic phase was then back extracted with water (10 ml, 2 vol) and the aqueous phase evaporated to afford a pale yellow solid (4.83 g, 80%). This solid (4 g) was dissolved in acetone (24 ml, 6 vol) and heated to reflux for one hour. The solution was allowed to cool down slowly to 0° C. at a rate of 5–10° C./hr. The crystals were filtered, washed with acetone (1.6 ml, 0.4 vol) and dried to give a white solid (3.23 g, 81%, >99.80/% e.e., 54 ppm Rh)

Purification of (S)-α-ethyl-2-oxo-1-pyrrolidine acetamide (Levetiracetam):

Levetiracetam obtained by asymmetric hydrogenation as described above (5 g, 98% e.e.) was recrystallised from acetone (30 ml, 6 vol) as above to yield a white crystalline solid (3.94 g. 81%, >99.8% e.e., 52 ppm Rh). This material (3 g) was recrystallised again as above to afford a white crystalline solid.(2.31 g, 77%, >99.8% e.e., 23 ppm Rh).

m.p, 118.4–119.9° C.

What is claimed is:

1. Process for preparing a compound of formula (B)

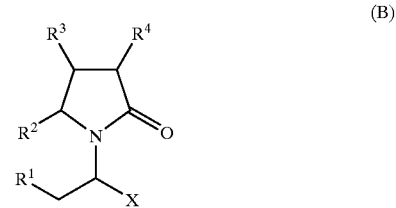

(B)

wherein

X is —CONR$^5$R$^6$ or —COOR$^7$ or —CO—R$^8$ or CN;

R$^1$ is hydrogen or alkyl, aryl, heterocycloalkyl, heteroaryl, halogen, hydroxy, amino, nitro, or cyano;

R$^2$, R$^4$ are the same or different and each is independently hydrogen or halogen, hydroxy, amino, nitro, cyano, acyl, acyloxy, sulfonyl, sulfinyl, alkylamino, carboxy, ester, ether, amido, sulfonic acid, sulfonamide, alkylsulfonyl, arylsulfonyl, alkoxycarbonyl, alkylsulfinyl, arylsulfinyl, alkylthio, arylthio, alkyl, alkoxy, oxyester, oxyamido, aryl, arylamino, aryloxy, heterocycloalkyl, heteroaryl, or vinyl;

$R^3$ is hydrogen, halogen, hydroxy, amino, nitro, cyano, acyl, acyloxy, sulfonyl, sulfinyl, alkylamino, carboxy, ester, ether, amido, sulfonic acid, sulfonamide, alkylsulfonyl, arylsulfonyl, alkoxycarbonyl, alkylsulfinyl, arylsulfinyl, alkylthio, arylthio, alkyl, alkoxy, oxyester, oxyamido, aryl, arylamino, aryloxy, heterocycloalkyl, heteroaryl, (C2–C5)alkenyl, (C2–C5)alkynyl, azido, or phenylsulfonyloxy;

$R^5$, $R^6$, $R^7$ are the same or different and each is independently hydrogen, hydroxy, alkyl, aryl, heterocycloalkyl, heteroaryl, alkoxy, or aryloxy; and $R^8$ is hydrogen, hydroxy, thiol, halogen, alkyl, aryl, heterocycloalkyl, heteroaryl, alkylthio, or arylthio;

each alkenyl, alkynyl, and azido may independently be optionally substituted by one or more halogen, cyano, thiocyano, azido, alkylthio, cyclopropyl, acyl, or phenyl;

which comprises reacting a compound of general formula (A), wherein $R^1$, $R^2$, $R^3$, $R^4$ and X have the same meanings defined above, according to the following Scheme (6):

Scheme (6)

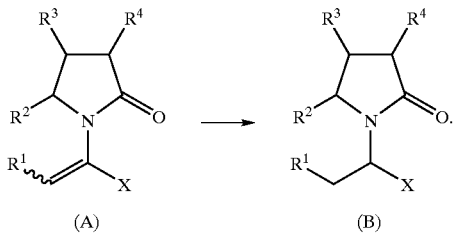

(A)     (B)

2. Process according to claim 1, which comprises catalytic hydrogenation of (A).

3. Process according to claim 1, wherein the compound of formula (A) is subjected to asymmetric hydrogenation using a chiral catalyst.

4. Process according to any one of claims 1 to 3, wherein $R^3$ is (C1–C5)alkyl, (C2–C5)alkenyl, (C2–C5)alkynyl, cyclopropyl, azido, phenyl, phenylsulfonyl, phenylsulfonyloxy, tetrazole, thiazole, thienyl, furyl, pyrrole or pyridine;

each alkyl, alkenyl, alkynyl, cyclopropyl, and azido may optionally be substituted by one or more halogen, cyano, thiocyano, azido, alkylthio, cyclopropyl, acyl, or phenyl; and any phenyl moiety may be substituted by one or more halogen, alkyl, haloalkyl, alkoxy, nitro, amino, or phenyl.

5. Process according to claim 1, wherein $R^1$ is methyl, $R^2$ and $R^4$ are H, $R^3$ is hydrogen, alkyl or haloalkenyl and X is —$CONH_2$ or —COOMe or —COOEt or —COOH.

6. Process according to claim 5, wherein $R^3$ is hydrogen, propyl or difluorovinyl.

7. Process according to claim 1, wherein the compound of formula (A) is a Z isomer or an E isomer.

* * * * *